United States Patent [19]

Zhang et al.

[11] Patent Number: 4,824,547

[45] Date of Patent: Apr. 25, 1989

[54] ELECTROPHORETIC EXTRACTION OF PROTEINS FROM TWO-DIMENSIONAL ELECTROPHORESIS GEL SPOTS

[75] Inventors: Jian-Shi Zhang, Shanghai, China; Carol S. Giometti, Glenview; Sandra L. Tollaksen, Montgomery, both of Ill.

[73] Assignee: The United States of America as represented by the United States Department of Energy, Washington, D.C.

[21] Appl. No.: 92,924

[22] Filed: Sep. 4, 1987

[51] Int. Cl.$^4$ ............................................. G01N 27/28
[52] U.S. Cl. ............................ 204/299 R; 204/182.8; 204/301
[58] Field of Search ................. 204/299 R, 301, 182.8

[56] References Cited

U.S. PATENT DOCUMENTS

| | | | |
|---|---|---|---|
| 3,506,554 | 3/1968 | Broome | 204/180 |
| 4,088,561 | 5/1978 | Anderson . | |
| 4,111,785 | 9/1978 | Roskam | 204/299 R |
| 4,169,036 | 9/1979 | Anderson et al. . | |
| 4,552,640 | 11/1985 | Kartenbeck | 204/301 |

OTHER PUBLICATIONS

Anderson et al., "Analytical Techniques for Cell Fractions", Anal. Biochem., 85, 341–354 (1978).
D. W. Cleveland et al., "Peptide Mapping by Limited Proteolysis in Sodium Dodecyl Sulfate and Analysis by Gel Electrophoresis", J. Biol. Chem., 252 (1977) 1102–1106.
C. S. Giometti et al., "Tropomyosin Heterogeneity in Human Cells", J. Biol. Chem. 259 (1984) 14113–14120.
P. H. O'Farrell, "High Resolution Two–Dimensional Electrophoresis of Proteins", J. Biol. Chem. 250 (1975) 4007–4021.
N. G. Anderson et al., "Two-Dimensional Analysis of Serum and Tissue Proteins: Multiple Isoelectric Focusing", Anal. Biochem. 85 (1978) 331–340.
N. L. Anderson et al., "Two-Dimensional Analysis of Serum and Tissue Proteins: Multiple Gradient–Slab Gel Electrophoresis", Anal. Biochem. 85 (1978) 341–354.
S. L. Tollaksen et al., "Operation of the Iso-Dalt System, Seventh Edition" Report, ANL-BIM-84-1, (1984), Argonne National Laboratory.

Primary Examiner—John F. Niebling
Assistant Examiner—Isabelle Rodriguez
Attorney, Agent, or Firm—James W. Weinberger; Thomas G. Anderson; Judson R. Hightower

[57] ABSTRACT

After two-dimensional electrophoresis of proteins or the like, resulting in a polyacrylamide gel slab having a pattern of protein gel spots thereon, an individual protein gel spot is cored out from the slab, to form a gel spot core which is placed in an extraction tube, with a dialysis membrane across the lower end of the tube. Replicate gel spots can be cored out from replicate gel slabs and placed in the extraction tube. Molten agarose gel is poured into the extraction tube where the agarose gel hardens to form an immobilizing gel, covering the gel spot cores. The upper end portion of the extraction tube is filled with a volume of buffer solution, and the upper end is closed by another dialysis membrane. Upper and lower bodies of a buffer solution are brought into contact with the upper and lower membranes and are provided with electrodes connected to the positive and negative terminals of a DC power supply, thereby producing an electrical current which flows through the upper membrane, the volume of buffer solution, the agarose, the gel spot cores and the lower membrane. The current causes the proteins to be extracted electrophoretically from the gel spot cores, so that the extracted proteins accumulate and are contained in the space between the agarose gel and the upper membrane. A high percentage extraction of proteins is achieved. The extracted proteins can be removed and subjected to partial digestion by trypsin or the like, followed by two-dimensional electrophoresis, resulting in a gel slab having a pattern of peptide gel spots which can be cored out and subjected to electrophoretic extraction to extract individual peptides.

19 Claims, 4 Drawing Sheets

ELECTROPHORETIC EXTRACTION OF PROTEINS FROM TWO-DIMENSIONAL ELECTROPHORESIS GEL SPOTS

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

FIELD OF THE INVENTION

This invention relates to the analytical separation and purification of proteins and related materials, such as peptides, for example. More specifically, this invention relates to a method and apparatus for the electrophoretic extraction of proteins and similar materials from gel spots which have been produced by two-dimensional electrophoretic separation of proteins or the like.

BACKGROUND OF THE INVENTION

Two-dimensional electrophoresis of proteins is dsscribed and illustrated in U.S. Pat. No. 4,088,561, issued May 9, 1978 upon the application of Norman L. Anderson, entitled APPARATUS FOR ELECTROPHORESIS SEPARATION, and also in U.S. Pat. No. 4,169,036, issued Sept. 25, 1979 upon the application of Norman G. and Norman L. Anderson, entitled SYSTEM FOR LOADING SLAB-GEL HOLDERS FOR ELECTROPHORESIS SEPARATION. Such U.S. Pat. Nos. 4,088,561 and 4,169,036, are hereby incorporated by refefence in their entirety into the present patent application. The purpose of electrophoretic separation is to separate and purify individual proteins from samples containing a multitude of different proteins. Such samples may be derived from numerous sources, such as animal or human tissues or body cells, bacteria, viruses, vaccines and the like. Electrophoretic separation is also applicable to protein subunits, such as peptides, or nucleic acids.

The first stage of the two-dimensional electrophoretic separation involves isoelectric focusing of the proteins, so as to separate them in accordance with their different isoelectric points. Different proteins carry different electrical charges when dispersed in a buffer solution. Isoelectric focusing is carried out by using an electrical current to propel the protein molecules through a rod made of polyacrylamide gel material, and containing a pH gradient generated by the inclusion of amphoteric molecules called ampholytes which are commercially available. In the isoelectric focusing, the electrical current causes each protein molecule to migrate through the gel rod until the protein molecule reaches a location where the pH is exactly the correct value to neutralize the electrical charge on the molecule. Thus, isoelectric focusing has the effect of separating the proteins with different electrical charges into discrete bands along the length of the gel rod, each band containing proteins having the same isoelectric point.

In the second stage of the two-dimensional electrophoresis, the proteins are separated in accordance with their different molecular weights, by electrophoresis of the proteins through a polyacrylamide gel slab, acting as a sieve, and preferably having a density gradient along the length of the slab, so that the density of the gel material increases along the length of the slab. Due to the density gradient, the gel slab has a porosity gradient which is inversely related to the density gradient, so that the pores in the gel become smaller and smaller along the length of the slab. Generally, the gel slab is cast or otherwise produced between two spaced glass plates. The gel rod from the first stage is extruded from its supporting tube. The extruded rod is spaghetti-like in form and consistency. The gel rod is pressed against the low-density end of the gel slab and is suitably held in place. An electrical voltage is then applied between buffer solutions at the opposite ends of the gel slab, whereupon the proteins migrate through the slab until the protein molecules are stopped by the smaller and smaller pores of the slab. The gel slab and the buffer solutions contain the anionic detergent sodium dodecyl sulfate, which binds to all of the proteins in the first dimension gel, conferring upon them all a negative charge. Thus, the isoelectric points of the proteins are not a factor in the second stage separation.

In the second stage separation, the different proteins of different molecular weights produce separate spots along the gel slab. Each spot contains a purified protein having a unique isoelectric point and a unique molecular weight. The gel slab is peeled away from the supporting plates, and the spots in the gel slab are rendered visible by known staining and destaining procedures whereby the proteins are selectively stained with a suitable dye, so that a protein map is produced on the gel slab. Photographs of the gel slab can be taken to record the protein map. Moreover, the protein map can be scanned with an optical densitometer to produce electronic signals, which can be stored in a computer for further processing and use.

The individual gel spots can be cut out or cored, using a glass tube or some other cutter, to form gel spot cores. Each core contains a pure protein. Each gel spot core contains only a limited amount of the particular protein. A multiplicity of identical gel spot cores can be produced by making a multiplicity of identical runs of the two-dimensional separation processes, to produce a multiplicity of identical protein maps on replicate gel slabs, from which identical gel spots can be cored.

SUMMARY OF THE INVENTION

One principal object of the present invention is to provide a new method and apparatus for extracting proteins and related materials from gel core spots, whereby a highly purified protein becomes available for further processing, analysis or use.

A further object is to provide such a new method and apparatus, whereby a high percentage yield is achieved in extracting the proteins or the like from the gel core spots.

Another object is to provide such a new and improved method and apparatus, whereby the proteins or the like can be extracted from the gel spot cores with great facility, and without changing the proteins or introducing contaminating materials.

To achieve these and other objects, the present invention provides a method of electrophoretically extracting proteins and related materials from gel spot cores, the method comprising the steps of providing an extraction tube having a chamber therein, placing the gel spot cores in a first portion of the chamber, placing an immobilizing gel in the first portion of the chamber for surrounding and immobilizing the gel spot cores therein, providing a buffer solution in a second portion of the chamber immediately adjacent to the first portion and with the buffer solution contacting the immobilizing gel, and causing an electrical current to flow in and along the chamber whereby proteins or related materials present in the gel spot cores are electrophoretically extracted therefrom and caused to collect in the buffer solution.

The gel spot cores preferably comprise polyacrylamide gel. The immobilizing gel preferably comprises agarose.

In the electrophoretic extraction, a positive electrical polarity is preferably provided between the buffer solution and the immobilizing gel.

Preferably, the extraction tube is generally vertical, and the buffer solution is located above the immobilizing gel.

The buffer solution preferably contains sodium dodecyl sulfate.

The present invention provides apparatus for extracting proteins and related materials from gel spot cores, the apparatus comprising an extraction tube having a chamber therein for receiving the gel spot cores in a portion of the chamber, the extraction tube and the chamber having first and second opposite ends, means including a first porous membrane for closing the first end of the chamber in the extraction tube, means including a second porous membrane for closing the second end of the chamber in the extraction tube, an immobilizing gel for surrounding and immobilizing the gel spot cores in said portion of the chamber, the immobilizing gel extending in the tube from the second membrane to a location spaced from the first membrane, the chamber having a space therein between the immobilizing gel and the first membrane, means affording a first buffer solution contacting the outside of the first membrane, means affording a second buffer solution contacting the outside of the second membrane, a third buffer solution filling the space between the first membrane and the immobilizing gel, and means including first and second electrodes contacting the first and second buffer solutions for causing the flow of an electrical current along the chamber in the extraction tube and between the first and second buffer solutions, whereby proteins or related materials present in the gel spot cores are electrophoretically extracted therefrom and caused to collect in the third buffer solution between the first membrane and the immobilizing gel.

The first and second membranes are preferably dialysis membranes.

The immobilizing gel preferably comprises agarose.

The first electrode preferably has a positive electrical polarity relative to the second electrode to produce a corresponding direction of the electrical current.

The gel spot cores preferably comprise polyacrylamide gel.

Preferably, the extraction tube is generally vertical, and the space containing the third buffer solution is above the immobilizing gel.

Preferably, the first, second and third buffer solutions are similar in composition. The buffer solutions preferably contain sodium dodecyl sulfate.

Initially, the extraction tube is preferably placed in a vertical position, with the lower end of the tube closed by the second membrane. A number of the gel spot cores are then dropped into the open upper end of the extraction tube. Melted agarose gel is poured into the tube so that the agarose surrounds and covers the gel spot cores. The agarose is allowed to cool, so that it sets into a hard gel, whereupon the upper portion of the extraction tube, above the agarose, is filled with the desired buffer solution. The first membrane is then employed to close the upper end of the tube. Sealed connections are then made between the upper and lower ends of the tube and respective first and second receptacles, in which the first and second buffer solutions are placed, so that the buffer solutions come into contact with the respective first and second membranes. An electrical voltage is applied between first and second electrodes, immersed in the first and second buffer solutions, so that an electrical current flows through the buffer solutions and through the chamber in the extraction tube. The current flows through the buffer solution in the tube and also through the agarose and the gel spot cores. The electrical current causes the negatively-charged protein-sodium dodecyl sulfate complexes in the gel spot cores to migrate electrophoretically out of the cores, through the agarose and into the buffer solution above the agarose, where the proteins are collected. The first or upper membrane has the effect of containing the proteins. Any excess buffer solution in the space between the agarose and the first membrane passes through the first membrane into the larger body of buffer solution, above the first membrane. By way of example, electrophoretic extraction of the proteins may be carried out by running the electrical current for about two hours at approximately 200 volts.

BRIEF DESCRIPTION OF THE DRAWINGS

Further objects, advantages and features of the present invention will appear from the following detailed description taken with the accompanying drawings, in which:

More specifically, FIG. 8A is a drawing made by copying a photograph of a gel spot map, resulting from two-dimensional electrophoretic separation of proteins in a sample derived from mouse liver cells, the numerous gel spots representing numerous different proteins.

FIG. 8B is a drawing made by copying a photograph of a gel spot map resulting from two-dimensional electrophoresis of a protein extracted from gel spot cores corresponding to one gel spot, indicated by the arrow in FIG. 8A.

FIG. 8C is a drawing made by copying a computer-generated plot of a gel spot map resulting from two-dimensional electrophoresis of the same protein indicated in FIG. 8A, after electrophoretic extraction and digestion with trypsin. The horizontal arrow indicates trypsin peptides. The vertical arrow indicates undigested protein.

DETAILED DESCRIPTION OF AN ILLUSTRATIVE EMBODIMENT

Figure 1:
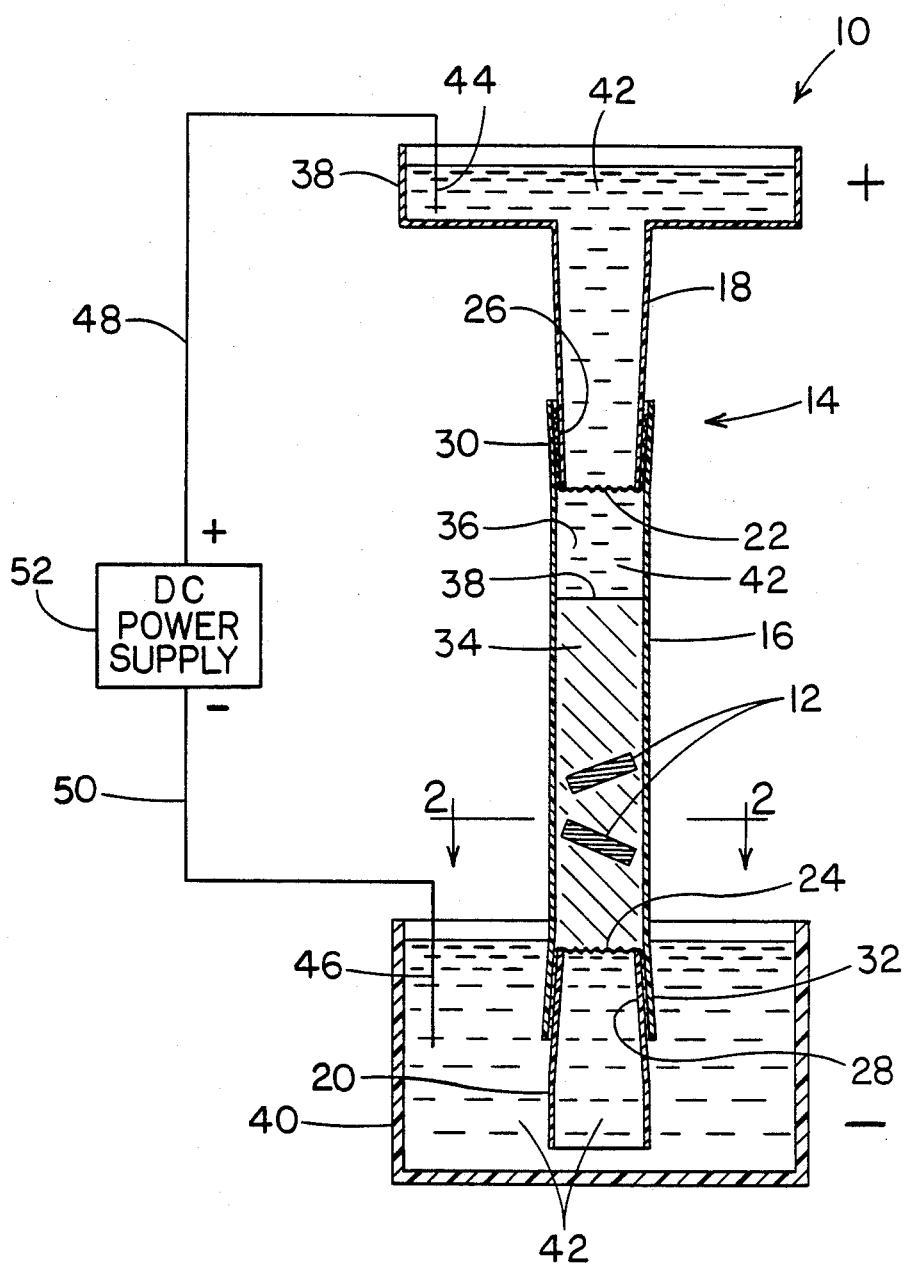
FIG. 1 is an enlarged schematic elevational section, taken centrally through an apparatus to be described as an illustrative embodiment of the present invention, such apparatus having the objective of electrophoretically separating proteins or the like from gel spot cores.

As previously indicated, FIG. 1 shows an illustrative embodiment of the present invention, in the form of apparatus 10 for electrophoretically separating proteins or similar materials from polyacrylamide gel spot cores 12, representing the results of two-dimensional electrophoresis (2DE) of biological samples containing proteins. FIG. 1 also illustrates the method of the present invention, which will be described in greater detail. The methods and apparatus employed in 2DE have already been summarized briefly in the preceeding portions of this application, and will be described in greater detail presently, in connection with FIGS. 3-8.

The gel spot cores 12 are generally in the form of flat round disks, cut or cored out from the flat gel slab employed in the second stage of 2DE. In this way, individual spots are cut away from the gel slab. Each gel spot core contains a small quantity of an individual protein having a unique isoelectric point and a unique molecular weight. The protein is present at a high level of purity. In principle, the gel spot cores could have some shape other than round. However, the gel spots can be cored out very easily by using a glass tube as a cutter. The glass tube may have a diameter of 2 millimeters or any other suitable size. Other cutters could be used.

Each gel spot core contains only a limited amount of the particular protein. To obtain a larger amount of protein, a multiplicity of identical gel spot cores can be produced by making a multiplicity of identical runs of the 2DE separation processes, so as to produce a multiplicity of protein maps on replicate gel slabs, from which identical gel spots can be cored.

To receive the gel spot cores 12, the apparatus 10 of FIG. 1 comprises an extraction tube assembly 14, including an extraction tube 16 and upper and lower end tubes 18 and 20, having sealing connections to the upper and lower ends of the extraction tube 16. While the extraction tube assembly 14 is shown in a vertical position, which is preferred, the assembly could be otherwise positioned, such as horizontally or at an inclined angle. The tubes 16, 18 and 20 are preferably made of a transparent plastic material, but could be made of other suitable materials, such as glass, for example. The material should be an electrical insulator. The diameter of the tubes 16, 18 and 20 may be approximately 2.5 millimeters, so that the apparatus 10 is adapted to carry out the electrophoretic separation on a microvolume basis. In FIG. 1, the aparatus 10 is shown diagrammatically and greatly enlarged, for clarity of illustration.

In he assembled aparatus 10, as shown in FIG. 1, the upper and lower ends of the extraction tube 16 are closed by upper and lower porous membranes 22 and 24, preferably dialysis membranes, which may have a molecular weight cutoff of approximately 3,500. As shown in FIG. 1, the membranes 22 and 24 are made of dialysis tubing, stretched across the ends of the upper and lower end tubes 18 and 20, which are then tightly fitted within the upper and lower ends of the extraction tube 16. As shown, the upper and lower tubes 18 and 20 have tapered ends 26 and 28 which are tightly fitted within slightly flared upper and lower ends 30 and 32 on the extraction tube 16. The dialysis tubing may be of a type known commercially as Spectra/Por 3.

In setting up the extraction apparatus 10, the lower membrane 24 is mounted across and around the tapered lower end 28 of the lower tube 20, which is then tightly inserted into the flared lower end 32 of the extraction tube 16, so as to form a sealed connection therewith, whereby the membrane 24 closes the lower end of the extraction tube 16. One or more gel spot cores 12 are then put into the extraction tube 16, which is capable of holding a considerable number of the cores 12. At this stage, the upper end of the extraction tube 16 is still open.

Heated agarose solution or the equivalent is then added to the extraction tube 16 and is allowed to cool, whereby the agarose solution sets or hardens to form an agarose gel 34 which immobilizes the gel spot cores 12, while also adjusting the volume of the space 36 which is formed between the upper membrane 22 and the upper surface 38 of the agarose gel 34, in the final extraction tube assembly 14. The extracted material is to be contained within the space 36, which may have a final volume ranging from 20 to 200 microliters, for example. The agarose solution may comprise 0.5% agarose, 0.1% sodium dodecyl sulfate (SDS), 24 millimole (mM) Trizma base, and 0.2 mole (M) glycine. Trizma, also known as Tris, is a commercially available buffer material, the chemical name of which is tris(hydroxymethyl)aminomethane-HCl. It will be understood that the composition of the agarose gel may be varied and that equivalent materials may be employed. In general terms, the agarose gel may be referred to as an immobilizing gel.

As shown in FIG. 1, an upper reservoir or container 38 connects with the upper end of the upper tube 18. The lower end of the lower tube 20 extends into a lower reservoir or container 40. Quantities of a buffer solution 42 are contained in the upper reservoir 38, the upper tube 18, the space 36 in the upper end of the extraction tube 16, the lower tube 20, and the lower reservoir 40. While there are three distinct quantities or volumes of the buffer solution 42, all three quantities preferably have the same composition. The buffer solution 42 may comprise 24 mM Trizma base, 0.2 M glycine, and 3.5 mM SDS, for example. It will be understood that the composition of the buffer solution may be varied and that equivalent materials may be employed.

The buffer solution 42 in the upper reservoir 38 is electrically contacted by an electrode 44, which has a substantial area immersed in the upper or first quantity of the buffer solution. Similarly, the second or lower quantity of the buffer solution 42, in the lower reservoir 40 is electrically contacted by a second or lower electrode 46 which has a substantial area immersed in the lower quantity of the buffer solution. The upper and lower electrodes 44 and 46 are connected to positive and negative supply leads or wires 48 and 50 extending from a direct current (DC) power supply 52, which may provide 200 volts or some other suitable voltage, so that electrophoresis is produced by the direct current through the extraction tube 16. The direct current flows through the third quantity of the buffer solution 42 in the space 36, so that electrophoresis causes the proteins in the gel spot cores 12 to migrate out of the cores 12, through the agarose gel 34 thereby causing the proteins to enter into the third quantity of the buffer solution 42 in the space 36. Upper membrane 22, prevents passage of the protein molecules from exiting space 36, while permitting passage of electrical current and buffer solution 42, so that any excess buffer solution flows through the membrane 22 into the upper tube 18. The protein molecules are contained and accumulated in the space 36.

To reach the extraction tube 16, the direct current passes through the positively polarized wire 48, the positive electrode 44, the first or upper volume of the buffer solution 42 in the upper reservoir 38 and the upper tube 18, and also through the membrane 22. In passing from the lower end of the extraction tube 16, the direct current passes through the lower membrane 24, the second or lower volume of the buffer solution 42 in the lower tube 20 and the lower reservoir 40, the negative electrode 46, and the wire 50, leading back to the power supply. Electrophoresis may be run for 2 hours at 200 volts, but it will be understood that the time and voltage may be varied. The general objective is to produce as much electrophoresis as necessary to extract the maximum amount of protein from the gel spot cores 12, so that the extracted protein will be accumulated in the space 36, where the protein will be available for further use or analysis.

The method and apparatus involved in the production of the gel spot cores by two-dimensional electrophoresis (2DE) will be described, with reference to FIGS. 3-7. A highly detailed description of 2DE is not necessary herein, because highly detailed descriptions of the various methods and apparatus involved are contained in the previously mentioned Norman L. Anderson Pat. No. 4,088,561 and the Norman G. and Norman L. Anderson Pat. No. 4,169,036, which have been incorporated herein by reference.

Figure 4:
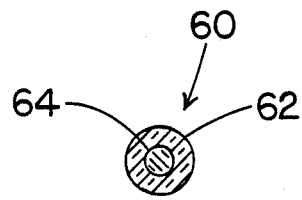
FIG. 4 is a cross section, taken generally along the line 4—4 in FIG. 3.
Figure 3:
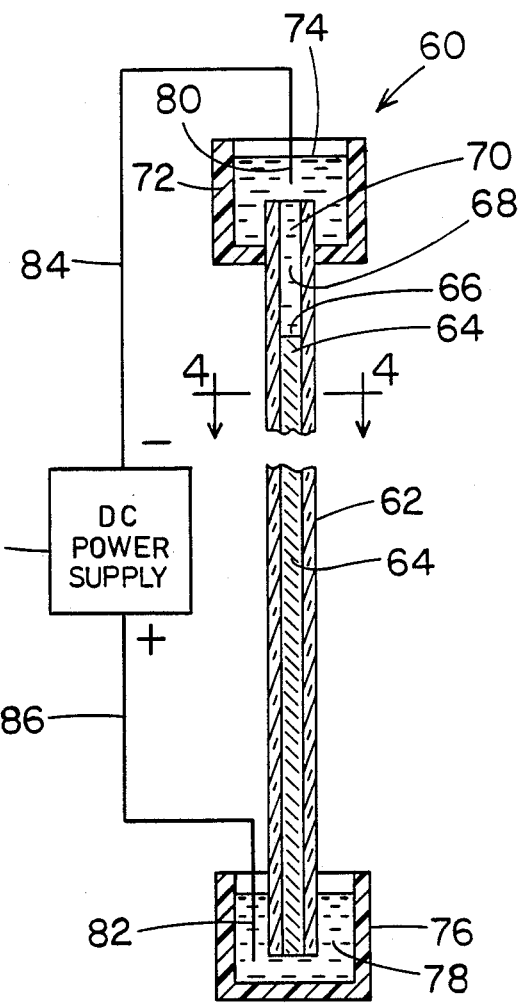
FIG. 3 is a diagrammatic longitudinal section showing the apparatus involved in the first stage of the two-dimensional separation of proteins or the like, in which the proteins are separated in accordance with their isoelectric points.

FIGS. 3 and 4 constitute diagrammatic illustrations of the isoelectric focusing apparatus 60 employed in the first stage of the 2DE. The apparatus 60 of FIGS. 3 and 4 comprises a glass tube 62 containing a rod 64 made of polyacrylamide gel material and containing a pH gradient generated by the inclusion of amphoteric materials called ampholytes, which are commercially available. The glass tube 62 could also be made of tansparent plastic or some other suitable material. The preparation of the gel rod 64 is described in detail in the previously mentioned Norman L. Anderson Pat. No. 4,088,561. FIGS. 3 and 4 illustrate only a single glass tube 62 and a single gel rod 64, but several tubes and rods are typically employed simultaneously in actual practice. The illustration of a single tube and rod is sufficient to illustrate the principles involved.

The illustrated gel rod 64 extends to the lower end of the glass tube 62, but the gel rod 64 has an upper surface 66 which is spaced well below the upper end of the glass tube 62, leaving a space 68 therein, in which the desired samples 70 may be placed. The samples 70 may comprise proteins or related materials, dispersed in an electrically conductive buffer solution.

The upper end of the glass tube 62 has a sealed connection with an upper reservoir or container 72, adapted to receive an electrically conductive buffer solution 74, after a sample 70 has been added to the space 68 in the upper end of the tube 62. The lower end of the glass tube extends into a lower reservoir or container 76, in which an electrically conductive buffer solution 78 is placed, so as to immerse the lower end of the tube 62 and the lower end of the gel rod 64. Upper and lower electrodes 80 and 82 are inserted into the reservoirs 72 and 76, so that the electrodes 80 and 82 have substantial areas in electrical contact with the buffer solutions 72 and 78. Electrically conductive wires or leads 84 and 86 extend between the respective electrodes 80 and 82 and the negative and positive terminals of a direct current (DC) power supply 88. The composition of the buffer solutions 74 and 78 and other details are described in the previously mentioned Norman L. Anderson Pat. No. 4,088,561.

In the isoelectric focusing apparatus 60 of FIGS. 3 and 4, the electrical voltage from the power supply 88 causes a direct current to flow through the wire 86, the electrode 82, the buffer solution 78, the sample 70, the gel rod 64, the buffer solution 74, the electrode 80 and the wire 84. The protein molecules in the sample 70 are caused to migrate electrophoretically along the gel rod 64 toward the positive electrode 82, or downwardly, in this instance. Different protein molecules carry different electrical charges when the molecules are dispersed in a buffer solution. The electrical current causes isoelectric focusing, in that each protein molecule is caused to migrate electrophoretically through the gel rod 64 until the protein molecule reaches a location where the pH is exactly the correct value to neutralize the electrical charge on the molecule. Thus, isoelectric focusing has the effect of separating the proteins with different electrical charges into discrete bands along the length of the gel rod 64. Each band contains proteins having the same isoelectric point.

Figures 5, 6:
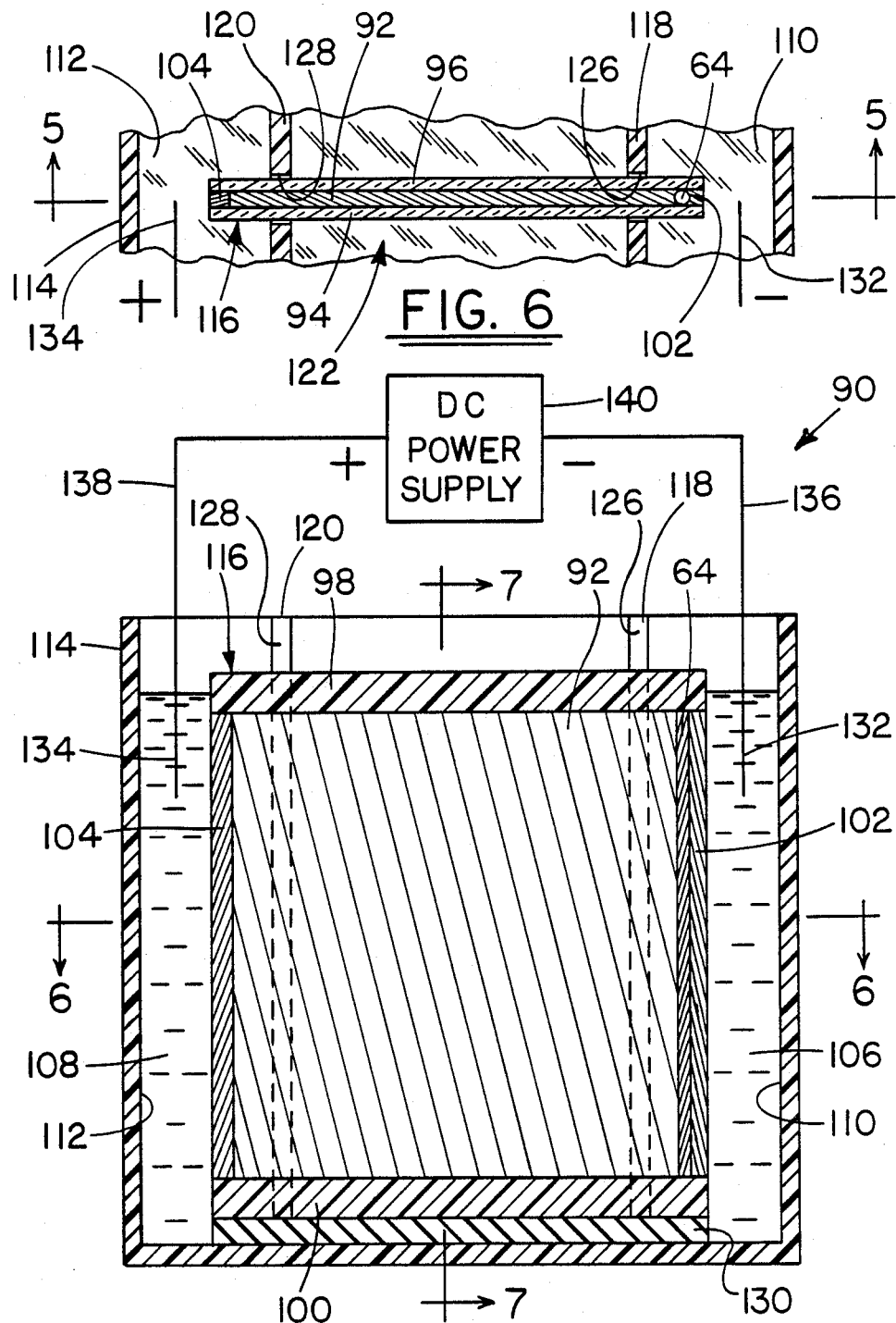
FIG. 5 is an elevational section, taken along the line 5—5 in FIG. 6, diagrammatically showing the apparatus involved in the second stage of the two-dimensional separation, in which the proteins or the like are separated in accordance with their molecular weight, by causing the proteins or the like to migrate by electrophoresis along a gel slab, sandwiched between two transparent plates.
FIG. 6 is a horizontal section, taken generally along the line 6—6 in FIG. 5.
Figure 7:
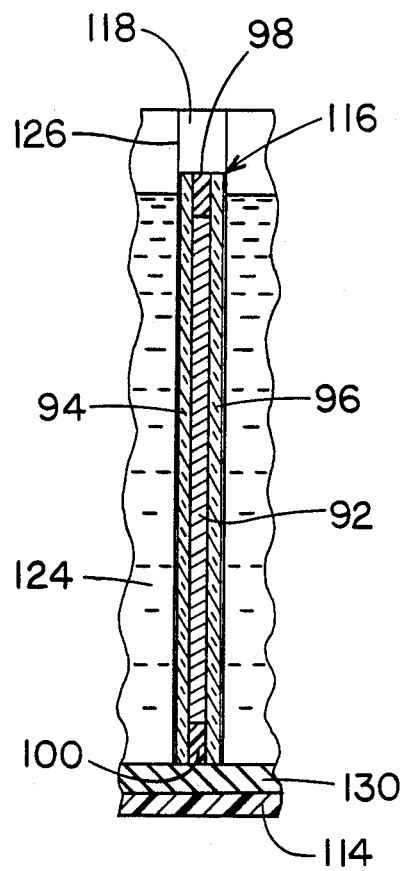
FIG. 7 is affragmentary vertical section, taken generally along the line 7—7 in FIG. 5.

FIGS. 5-7 comprise diagrammatic illustrations of the second stage apparatus 90 for 2DE. The second stage of 2DE is described in detail in the previously mentioned Norman L. Anderson Pat. No. 4,088,561, and also in the previously mentioned Norman G. and Norman L. Anderson Pat. No. 4,169,036. In the second stage apparatus 90, the proteins are separated in accordance with their different molecular weights, by electrophoresis of the proteins through a polyacrylamide gel slab 92, acting as a sieve and preferably having a density gradient along the length of the slab, so that the density of the gel material increases along the length of the slab, from right to left as shown in FIGS. 5 and 6. Due to the density gradient, the gel slab 92 has a porosity gradient, which is inversely related to the density gradient, so that the pores in the gel become smaller and smaller along the length of the slab, from right to left, as shown in FIGS. 5 and 6.

As shown in FIGS. 5-7, the polyacrylamide gel slab 92 is cast or otherwise produced between two spaced glass plates 94 and 96 which afford mechanical support and electrical insulation. The plates 94 and 96 may be made of some other insulating material, such as transparent plastic. Spacers 98 and 100 are preferably provided between the plates 94 and 96 along their upper and lower edge portions, as shonn in FIGS. 5 and 7. The spacers 98 and 100 are preferably in the form of electrically insulating strips, made of plastic or some other suitable material, and secured to the plates by a suitable adhesive, which also seals the joints between the plates and the spacers.

The polyacrylamide gel material in the slab 92 is preferably cast or otherwise formed with a density gradient along the length of the slab 92, extending from right to left in FIGS. 5 and 6. For example, the density of the slab 92 may increase linearly from 9% to 17% of the polyacrylamide gel, between the right hand end and the left hand end of the slab, as shown in FIGS. 5 and 6. The previously mentioned U.S. Pat. No. 4,169,036 of Norman G. Anderson and Norman L. Anderson contains a detailed description and illustrations of methods and apparatus employed for producing such gel slabs having density gradients.

After the isoelectric focusing has been completed in the first stage apparatus 60 of FIGS. 3 and 4, the gel rod 64 is extruded from its supporting tube 62. The extrusion can easily be accomplished by removing the tube 62 from the apparatus 60 and supplying water or other fluid pressure to the upper end of the tube 62. The extruded gel rod 64 is spaghetti-like in form and consistency. The gel rod 64 is pressed against the low density end of the gel slab 92, such end being the right hand end in FIGS. 5 and 6. It will be seen that the gel rod 64 engages the right hand end of the gel slab 92 and is confined between the glass plates 94 and 96. The gel rod 64 is suitably held in place, as by means of an electrically conductive stacking gel or filler 102, as shown in FIGS. 5 and 6. The gel rod 64 may be otherwise held in place. A similar filler 104 is shown between the glass plates 94 and 96 along the left hand end of the gel slab 92 in FIGS. 5 and 6, but may be omitted or replaced with other means.

In the second stage apparatus 90 of FIGS. 5–7, an electrical voltage is applied between electrically conductive buffer solutions 106 and 108 at the opposite ends of the gel slab 92, so that an electrical current will flow through the gel slab, whereby the protein molecules are caused to migrate by electrophoresis through the gel slab 92, until the protein molecules are stopped by the smaller and smaller pores of the slab, acting in the manner of a sieve. The gel slab 92 and the buffer solutions 106 and 108 contain the anionic detergent sodium dodecyl sulfate (SDS), or the equivalent, which binds to all of the proteins in the first dimensional gel rod 64, thereby conferring a negative charge upon all such proteins. Thus, the isoelectric points of the proteins are not a factor in the second stage separation.

As shown in FIGS. 5–7, the buffer solutions 106 and 108 are contained within electrically isolated end compartments 110 and 112 of a partitioned tank or other receptacle 114, preferably made of a transparent plastic material or other suitable electrically insulating material.

The second stage apparatus 90 and particularly the tank 114 are preferably of the construction illustrated and described in detail in the previously mentioned Norman L. Anderson Pat. No. 4,088,561. The tank 114 is adapted to receive a plurality of the gel slab holder assemblies 116, one of which is illustrated in FIGS. 5–7, comprising the gel slab 92, the glass plates 94 and 96 and associated components, so that electrical currents can be supplied to several gel slabs simultaneously. The tank 114 has two slotted partitions 118 and 120 which provide the needed electrical isolation for the end compartments 110 and 112, while also providing a central compartment 122 containing additional buffer solution 124 which is used as a coolant, to assist in dissipating the heat which is produced in each gel slab 92 by the passage of electrical current through the slab. The partitions 118 and 120 isolate the central compartment 122 electrically from the end compartments 110 and 112. As shown in FIGS. 5–7, the gel slab holder assembly 116 is sealingly received in slots 126 and 128, formed in the partitions 118 and 120. The joints between the assembly 116 and the partitions 118 and 120 are suitably sealed against the passage of any electrical current or the buffer solutions. The lower edge of the assembly 116 is in sealing engagement with a bottom sealing member or pad 130, made of a soft resilient electrically insulating material, such as a suitable synthetic rubber-like material.

As shown in FIGS. 5 and 6, electrodes 132 and 134 extend into the buffer solutions 106 and 108 and have substantial areas in electrical contact with the buffer solutions, which are in the end compartments 110 and 112 of the tank 114. Wires or leads 136 and 138 extend between the respective electrodes 132 and 134 and the negative and positive terminals of a direct current (DC) power supply 140. The electrophoresis in the gel slab 92 is produced by an electrical current which flows through the wire 138, electrode 134, the buffer solution 108, the filler 104, the gel slab 92, the gel rod 64, the filler 102, the buffer solution 106, the electrode 132 and the wire 136. The negative charges on the protein molecules in the gel rod 64 cause them to migrate electrophoretically through the gel slab 92, toward the positive electrode 134, until the molecules are stopped by the smaller and smaller pores in the gel slab 92 acting as a selective sieve, due to the density gradient of the gel in the slab 92. The migratory direction of the protein molecules is horizontal from right to left, when the gel slab 92 is oriented as shown in FIG. 5. The migratory distance of the protein molecules is inversely related to their molecular weights, so that the proteins having smaller molecular weights travel farther to the left than the proteins having larger molecular weights. The proteins are thus separated in accordance with their molecular weights.

It will be recalled that the different protein molecules in the original sample were separated in the first stage apparatus 60 (FIG. 3) into discrete bands distributed along the vertically oriented length of the gel rod 64, each of the bands containing proteins having a unique isoelectric point, different from the isoelectric points of the other bands. In the second stage apparatus 90 of FIGS. 5–7, the proteins in each discrete band are spread out horizontally by electrophoresis through the gel slab 92, and are separated according to the different molecular weights of the proteins, into discrete gel spots, each of which contains a substantially pure protein, having a unique combination of a particular isoelectric point and a particular molecular weight.

Figure 2:
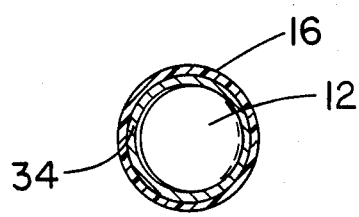
FIG. 2 is the horizontal cross section taken through the extraction tube, generally along the line 2—2 in FIG. 1.

After the second stage electrophoresis has been completed, the gel slab holder assembly 116 is removed from the tank 114, and the gel slab 92 is peeled away from the glass plates 94 and 96. The gel spots can be and preferably are rendered visible by known or suitable staining and destaining techniques. For example, the proteins can be stained by a commercially available dye known as Coomassie Blue R250 in 0.5% phosphoric acid, ($H_3PO_4$) with 50% ethanol, and then destained in 20% ethanol. By these staining and destaining processes, the proteins in the gel spots are given a visible blue color. Gel spot cores can be obtained by soaking the stained gel slab 92 in distilled water for a minimum of 1 hour, following which the gel spots can be cored out by using a suitable cutter, such as a glass tube having a diameter of 2 millimeters. Any number of replicate gel spot cores can be obtained by cutting out the same gel spot from replicate gel slabs. The replicate gel spot cores contain the same pure protein, which can be extracted from the gel spot cores by using the electrophoretic extraction apparatus 10, in accordance with the method described in connection with FIGS. 1 and 2.

The stained gel spots on the gel slab 92, resulting from 2DE, produce a protein map which can be photographed to provide a permanent record. Moreover, the protein map can be scanned with an optical densitometer, to produce electronic signals which can be stored in a computer for further processing and use.

FIG. 8A is a drawing made by copying a photograph of a gel spot protein map, resulting from 2DE of proteins in a sample derived from mouse liver cells. The numerous gel spots represent numerous different proteins which were present in the original sample.

The protein map represented in FIG. 8A was produced by 2DE in which the first dimension or stage was carried out with isoelectric focusing in 10-inch gel rods containing commercially available amphoteric materials or ampholytes comprising 50% Biolytes, having pH 3-10, and 50% Biolytes, having pH 5-7. The isoelectric focusing was carried out for 30,000 volt-hours. The second dimension, involving sodium dodecyl sulfate polyacrylamide gel electrophoresis (SDS-PAGE) was done on a gel slab having a linear gradient density of 9-17% polyacrylamide gels.

The arrow in FIG. 8A indicates a protein gel spot which was cored out. The protein was then extracted using the apparatus of FIGS. 1 and 2, in accordance with the method described in connection with FIGS. 1 and 2. In order to verify that the extracted protein was a substantially pure protein, the extracted protein was made the subject of 2DE, resulting in a protein map shown in FIG. 8B, which is a drawing made by copying a photograph of the gel spot map resulting from the 2DE of the extracted protein. It will be seen that FIG. 8B shows only one protein gel spot, which is substantially the same as the gel spot indicated by the arrow in FIG. 8A.

The substantially pure protein extracted from a particular gel spot core, or replicate cores from replicate gel slabs, may be subjected to proteolysis or digestion by a protease enzyme, such as trypsin, to produce peptides. In one case, for example, aliquots of the extracted protein were mixed with 2-5 micrograms/5 microliters trypsin and kept at room temperature for 30 minutes. The reaction was stopped by addition of equal volume of 0.5 M cyclohexylaminoethane sulfonic acid (CHES) (pH 9.5), 2% SDS, 1% dithiothreitol, and 10% glycerol. Aliquots of the extracted proteins without treatment with trypsin were also mixed with an equal volume of the CHES solution.

Both the aliquots of enzyme-cleaved (digested) extracted protein and the aliquots of uncleaved (undigested) extracted protein were subjected to separate runs of 2DE, carried out as described in connection with FIGS. 3-7. The first-dimension isoelectric focusing was carried out in 7-inch gel rods containing a mixture of the following commercially available ampholytes: 40% Servalyt pH 3-10; 40% Pharmalyte pH 3-10; and 20% Pharmalyte pH 5-8. The aliquots of peptides and proteins were focused for 14,000 volt-hours. The second-dimension SDS-PAGE was done on gel slabs having a linear density gradient of 9-17% polyacrylamide gels, but without equilibration of the first-dimension gel rods before loading them on the gel slabs for the second-dimension SDS-PAGE. The gel slabs were peeled from the supporting plates, and the peptides were detected or rendered visible by well known silver staining procedures.

The resulting peptide gel spot map is illustrated in FIG. 8C, which is a drawing made by copying a computer-generated plot of a gel spot map resulting from 2DE of the same protein, represented in FIG. 8B, after electrophoretic extraction and digestion with trypsin, as just described. The horizontal arrow in FIG. 8C indicated trypsin peptides. The vertical arrow indicates undigested protein, in substantially the same location as in FIG. 8B. It will be recalled that FIG. 8B is a drawing made by copying a photograph of the gel spot map resulting from 2DE of the undigested protein, extracted from the same gel spot, indicated by the arrow in FIG. 8A.

Tests have been conducted to determine the percentage recovery of electrophoretically extracted proteins from gel spots. The method used was to tag or label the original protein samples with a radioactive isotope, so that the protein concentrations could be measured with a radiation counter. In such tests, the initial protein samples were made up using cells of a commercially available microorganism known as V79, labeled with $^{35}S$-methionine, which is a compound containing radioactive sulfur. The cells were harvested with a solution containing 9 M urea, 4% NP40, 5% mercaptoethanol, and 2% ampholytes (pH 9-12, LKB). The resulting sample was made the subject of 2DE, performed as described in connection with FIGS. 3-7. Eight different gel spots from one gel slab were then cored out. Each gel spot core was then made the subject of electrophoretic extraction, as illustrated and described in connection with FIGS. 1 and 2. The same 8 gel spots were cored out from a duplicate gel slab. Each gel spot core of the duplicate set was separately extracted by mixing each gel spot core with 3 milliliters 30% hydrogen peroxide ($H_2O_2$), and heating the mixture at 110° C. for 1.5 hours. The protein concentrations in both the unextracted gel spot cores and the extracted proteins were measured, using a radiation counter. Such protein concentration measurements were made as to both the electrophoretically extracted proteins and the $H_2O_2$-extracted proteins. In each case, the proteins were mixed with 10 milliliters Aquasol-2 universal liquid scintillation cocktail, obtained commercially from New England Nuclear. The mixture was counted with a Beckman liquid scintillation counter.

The following table shows the percentage of protein recovered by the electrophoretic extraction of proteins from the gel spot cores. An average recovery of approximately 70% was obtained. More specifically, the following table shows the counts per minute (CPM) of each of the 8 gel spots; the CPM of the extracted protein from the corresponding gel spots; and the percentage recovery in each case.

| Spot Numbers | 1 | 2 | 3 | 4 | 5 | 6 | 7 | 8 |
| --- | --- | --- | --- | --- | --- | --- | --- | --- |
| CPM of gel spot | 1681 | 1035 | 1617 | 854 | 12633 | 2778 | 3336 | 24063 |
| CPM of extraction | 706 | 838 | 1156 | 547 | 11315 | 1888 | 2883 | 13408 |

-continued

| Spot Numbers | 1 | 2 | 3 | 4 | 5 | 6 | 7 | 8 |
|---|---|---|---|---|---|---|---|---|
| Recovery (%) | 42.0 | 81.0 | 71.5 | 64.1 | 89.6 | 68.0 | 86.4 | 55.7 |

The average recovery is 69.8%.

Figure 8:
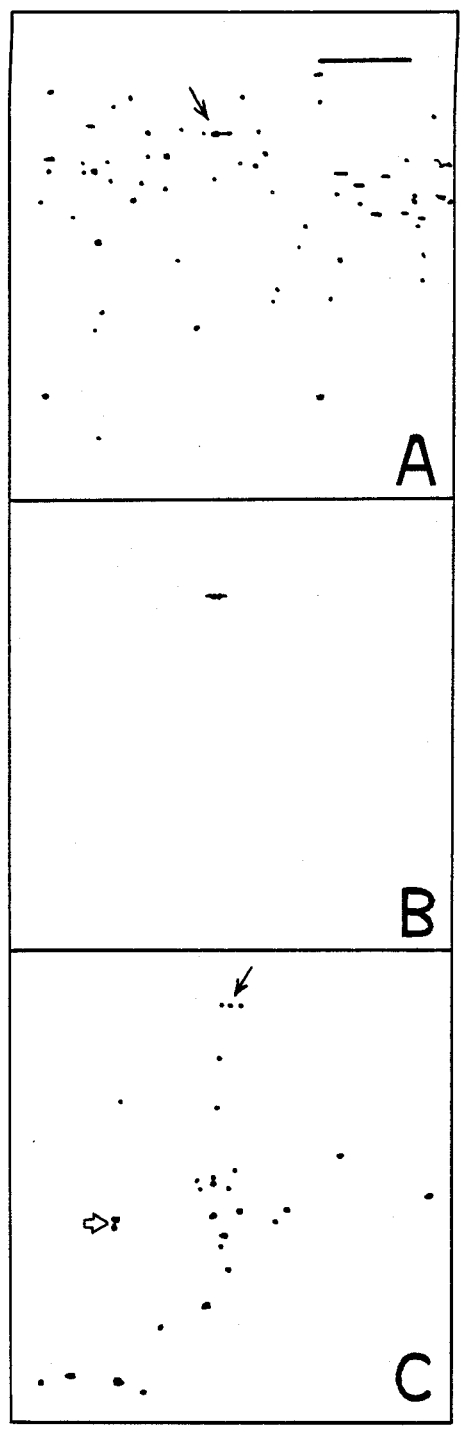
FIG. 8 comprises reproductions of gel spot maps produced on gel slabs and resulting from two-dimensional electrophoretic separation of proteins and peptides.

As previously indicated, FIG. 8 shows a comparison of the original 2DE pattern (FIG. 8A) of mouse liver proteins with the 2DE pattern of extracted proteins, with and without trypsin digestion. The gel spot that was used for the extraction procedure is indicated by the arrow in FIG. 8A. FIG. 8B is the 2DE pattern of the electrophoretically extracted protein from 5 identical spot cores from replicate gels. The slight charge-shift modification observed in the pattern is probably due to the staining-destaining procedure used for protein detection after the first 2DE separation. FIG. 8C shows the peptide pattern after 2DE of a comparable amount of the electrophoretically extracted protein from the same gel spot as shown in FIG. 8B, after cleavage (digestion) with trypsin.

The present invention provides a simple yet effective method and apparatus for extracting proteins from polyacrylamide gels. A high percentage yield is achieved in the extraction process. The method and apparatus of the present invention can be applied not only to proteins, but also to related materials, such as peptides, for example. After extraction, the proteins are dispersed in a small volume of a buffer solution, so that it is easy to use the extracted proteins for further processing, analysis or other use. The extracted proteins can be subjected to partial proteolysis, involving digestion by trypsin or the like, followed by 2DE to produce a peptide gel spot map in the second-dimension gel slab. This method is useful for the biochemical characterization of individual proteins in 2DE gel spot patterns, and for the identification of both similarities and differences between a pair of related protein spots. Because the number of gel spots to be extracted and the extraction volume can be adjusted in the extraction method and apparatus of the present invention, differences in the primary structure of both abundant and minor proteins can be investigated. By extracting protein from 10 or more replicate gel spots, enough protein can be obtained to allow amino acid sequencing of peptides that carry significant amino acid differences. The differences between normal and mutated proteins can be detected and investigated.

Various modifications, alternative constructions and equivalents may be employed, without departing from the true spirit and scope of the invention, as described above and as defined in the following claims.

We claim:

1. Apparatus for extracting proteins and related materials from gel spot cores, the apparatus comprising
   an extraction tube having a chamber therein for receiving the gel spot cores in a portion of the chamber,
   the extraction tube and the chamber having first and second opposite ends,
   means including a first porous membrane for closing the first end of the chamber in the extraction tube,
   means including a second porous membrane for closing the second end of the chamber in the extraction tube,
   an immobilizing gel for surrounding and immobilizing the gel spot cores in said portion of the chamber,
   the immobilizing gel extending in the tube from the second membrane to a location spaced from the first membrane,
   the chamber having a space therein between the immobilizing gel and the first membrane,
   means affording a first buffer solution contacting the outside of the first membrane,
   means affording a second buffer solution contacting the outside of the second membrane,
   a third buffer solution filling the space between the first membrane and the immobilizing gel,
   and means including first and second electrodes contacting the first and second buffer solutions for causing the flow of an electrical current along the chamber in the extraction tube and between the first and second buffer solutions,
   whereby proteins or related materials present in the gel spot cores are extracted therefrom and are caused to collect in the third buffer solution between the first membrane and the immobilizing gel.

2. Apparatus according to claim 1,
   in which the first and second membranes are dialysis membranes.

3. Apparatus according to claim 1,
   in which the immobilizing gel comprises agarose.

4. Apparatus according to claim 1,
   in which the first electrode has a positive electrical polarity relative to the second electrode to produce a corresponding direction of the electrical current.

5. Apparatus according to claim 1,
   in which the gel spot cores comprise polyacrylamide gel.

6. Apparatus according to claim 1,
   in which the extraction tube is generally vertical,
   and the space containing the third buffer solution is above the immobilizing gel.

7. Apparatus according to claim 1,
   in which the first, second and third buffer solutions are similar in composition.

8. Apparatus according to claim 7,
   in which the buffer solutions contain sodium dodecyl sulfate.

9. A method of extracting proteins and related materials from gel spot cores comprising:
   providing an extraction tube having a chamber therein, the tube having first and second opposite ends;
   providing first and second porous membranes for closing the first and second ends of the extraction tube respectively;
   placing the gel spot cores in a first portion of the chamber;
   placing an immobilizing gel in the first portion of the chamber for surrounding and immobilizing the gel spot cores therein, the gel extending in the tube from the second membrane to a location spaced from the first membrane to form a second portion of the chamber in the space therebetween;
   providing a buffer solution in the second portion of the chamber between the gel and the first membrane;

providing additional bodies of buffer solution to contact the opposite sides of the membranes from the first mentioned buffer solution and the immobilizing gel; and causing an electrical current to flow between the additional bodies of buffer solution in and through the chamber, whereby proteins or related material present in the gel spot cores are extracted therefrom and caused to collect in the first-mentioned buffer solution.

10. A method according to claim 9,
in which the gel spot cores comprise polyacrylamide gel.

11. A method according to claim 9,
in which the immobilizing gel comprises agarose.

12. A method according to claim 9,
in which a positive electrical polarity is provide between the buffer solution and the immobilizing gel.

13. A method according to claim 9,
in which the extraction tube is generally vertical,
and the buffer solution is located above the immobilizing gel.

14. A method according to claim 9,
in which the buffer solution contains sodium dodecyl sulfate.

15. A method of analyzing a sample containing proteins, the method comprising the steps of:

running the sample through two-dimensional electrophoresis resulting in a polyacrylamide gel slab having the proteins in a pattern of gel spots;

coring out a particular gel spot and thereby producing a gel spot having a particular protein therein;

providing an extraction tube having a chamber therein;

providing first and second dialysis membranes to close opposite ends of the chamber in the extraction tube;

placing the gel spot in a first portion of the chamber;

placing an immobilizing gel in the first portion of the chamber for surrounding and immobilizing the gel spot core therein;

providing a buffer solution in a second portion of the chamber between the immobilizing gel and the dialysis membrane and with the buffer solution contacting the immobilizing gel;

providing additional bodies of buffer solution to contact the opposite sides of the membranes from the first mentioned buffer solution and the immobilizing gel;

causing an electrical current to flow between the additional bodies of buffer solution in and through the chamber whereby the protein in the spot gel core is extracted electrophoretically therefrom and is caused to collect in the first-mentioned buffer solution as an extraction product;

subjecting the extraction product to proteolysis using a protein digesting agent and thereby producing a digested extraction product; and running at least one digested extraction product through at least one two-dimensional electrophoresis and thereby producing at least one additional polyacrylamide gel slab having peptides in a pattern of peptide gel spots.

16. A method according to claim 15
in which the immobilizing gel comprises agarose.

17. A method according to claim 15,
in which the protease digesting agent comprises trypsin.

18. A method according to claim 15,
comprising the steps of providing replicate samples containing the same proteins, running the replicate samples through replicate procedures of two-dimensional electrophoresis resulting in replicate polyacrylamide gel slabs having identical patterns of protein gel spots, coring out replicate individual protein gel spots from the replicate gel slabs and thereby producing replicate individual gel spot cores, and placing the replicate gel spot cores in the chamber of the extraction tube along with the first-mentioned gel spot core for simultaneous electrophoretic extraction of replicate proteins from all of the gel spot cores.

19. A method according to claim 15,
including the additional steps of coring out an individual peptide gel spot from at least one additional gel slab and thereby producing at least one peptide gel spot core, and electrophoretically extracting a peptide from the peptide gel spot core.

* * * * *